(12) United States Patent
Matsumoto

(10) Patent No.: US 7,383,965 B2
(45) Date of Patent: Jun. 10, 2008

(54) BLOOD-COLLECTION TUBE PREPARATION DEVICE

(75) Inventor: Toshikazu Matsumoto, Yokohama (JP)

(73) Assignee: Techno Medica Co., Ltd., Kanagawa (JP)

( * ) Notice: Subject to any disclaimer, the term of this patent is extended or adjusted under 35 U.S.C. 154(b) by 169 days.

(21) Appl. No.: 10/477,623

(22) PCT Filed: Mar. 25, 2002

(86) PCT No.: PCT/JP02/02849

§ 371 (c)(1),
(2), (4) Date: Nov. 12, 2003

(87) PCT Pub. No.: WO02/092437

PCT Pub. Date: Nov. 21, 2002

(65) Prior Publication Data

US 2004/0159589 A1     Aug. 19, 2004

(30) Foreign Application Priority Data

May 15, 2001   (JP)   ............................. 2001-144918
May 15, 2001   (JP)   ............................. 2001-144942

(51) Int. Cl.
*B65G 59/00* (2006.01)

(52) U.S. Cl. ................. 221/113; 209/518; 221/76; 235/456; 235/494; 235/375

(58) Field of Classification Search ............... 209/3.3, 209/583, 524, 517, 518; 235/375, 456, 494, 235/487; 156/384, 387, 556, 566, 569; 221/76, 221/113; 198/867.1, 867.11, 803.1, 803.13, 198/803.14

See application file for complete search history.

(56) References Cited

U.S. PATENT DOCUMENTS

| 2,799,173 | A | * | 7/1957 | Baird | .......................... 74/152 |
| 5,401,110 | A | * | 3/1995 | Neeley | ....................... 400/621 |
| 5,508,499 | A | * | 4/1996 | Ferrario | ....................... 235/375 |
| 5,688,361 | A | * | 11/1997 | Itoh | ........................... 156/362 |
| 5,893,263 | A | * | 4/1999 | Matsumoto et al. | ........ 156/387 |

FOREIGN PATENT DOCUMENTS

JP     07213586 A  *  8/1995
JP     11281651 A  *  10/1999

* cited by examiner

*Primary Examiner*—Kaitlin Joerger
(74) *Attorney, Agent, or Firm*—Lucas & Mercanti, LLP

(57) ABSTRACT

In the blood-sampling-tube preparation device according to the present invention, the each blood-sampling-tube containing section is provided with a number of compartments along a periphery thereof, in which the blood-sampling-tubes are contained one by one in a laying state, and an opening portion at a lower portion thereof for discharging the blood-sampling-tube from the each compartment, the compartments in each of the blood-sampling-tube containing section are intended to be moved in a peripheral direction thereof so that the blood-sampling-tube contained in the compartment aligned with the opening portion falls through the opening portion by moving the compartments at a suitable distance along the peripheral direction, and the blood-sampling-tube transferring means is arranged under the opening portions of the blood-sampling-tube containing sections for receiving the blood-sampling-tube felt from the each blood-sampling-tube containing section. Therefore, it is not necessary to provide a complicated mechanism for taking out the blood-sampling-tube from the blood-sampling-tube containing section. And therefore, the blood-sampling-tube preparation device can be structurally simplified and miniaturized (FIG. 2).

12 Claims, 9 Drawing Sheets

BLOOD-COLLECTION TUBE PREPARATION DEVICE

FIELD OF THE INVENTION

The present invention relates to an improvement of a blood-sampling-tube preparation device in which one or more blood-sampling-tubes are automatically selected from blood-sampling-tube containing sections that contain the intended kind of the blood-sampling-tubes, respectively, and a label with printed information data related to a patient corresponding to the selected tubes is automatically pasted on each of the selected tubes, and then the tubes with the label pasted for every patients are contained.

BACKGROUND OF THE ART

In the operation of testing a blood sample, the sample of one patient is typically examined for a number of test items. Therefore, in the hospital, the kinds of the blood-sampling-tubes are changed depending on the test items, and a worker writes the full names of the patients or the like on labels and pastes each of the labels on the blood-sampling-tubes in order to identify the test items and the patient name corresponding to the blood-sampling-tube at the blood test.

However, above-mentioned works such that a worker writes the name of the patient on the label and pastes the label on the each of the blood-sampling-tubes are very complicated. In addition, if a human carries out the works, a serious mistake that the label is pasted on the unintended blood-sampling tube or the like may occur.

In order to the above problems, the inventor of the present invention previously invented a blood-sampling-tube preparation device (Japanese Patent No. 2834595). In this device, at least two kinds of blood-sampling-tubes are contained within tube containing sections according to the kinds of the blood-sampling tubes, respectively. And one or more blood-sampling-tubes are selected and taken out from the corresponding tube containing section. And information data related to the patient corresponding to the blood-sampling-tube(s) taken out from the tube containing sections are printed on one or more labels. And then each of the labels is pasted on the blood-sampling-tube(s). And finally, one or more label pasted tubes for every patient are collected into a tube collection means.

After the inventor invented the above-mentioned device, the inventor and the third parties in various ways had improved the blood-sampling-tube preparation device. And improved devices had been proposed.

Most of conventional blood-sampling-tube preparation devices have the blood-sampling-tube requires sections for containing the blood-sampling-tubes on which the label is not pasted according to the blood test items. And in the blood-sampling-tube containing sections, the number of the blood-sampling-tubes are directly accumulated in the laying state. And the blood-sampling-tubes required for the blood tests are taken out one by one from a lump of the blood-sampling-tubes accumulated directly.

However, it is very difficult to take out the blood-sampling-tubes one by one from the lump of the blood-sampling-tubes accumulated directly. Because of this reason, the conventional device comprises a complicated mechanism for only taking out the blood-sampling-tube from the blood-sampling-tube containing section. And by reason of said complicated mechanism, the size of the device becomes big. In addition, by reason of said complicated mechanism, the production of the blood-sampling-tube preparation device becomes complicated, so that a price of the device had increased. Further, there is a disadvantage that the complicated mechanism causes any breakdown of the device.

SUMMARY OF THE INVENTION

It is an object of the present invention to solve the above-mentioned problems and provide the blood-sampling-tube preparation device that the provision of a complicated mechanism is not required for taking out the blood-sampling-tube from the blood-sampling-tube containing section.

To achieved the above object, the blood-sampling-tube preparation device according to the present invention, comprises at least two blood-sampling-tube containing sections, each of the sections being intended to contain same kind of blood-sampling-tubes according to sorts thereof, said each tube having a label pasted thereto, a label printing and pasting unit for printing information data related to a patient on the label and for pasting the printed label on the blood-sampling-tube, a blood-sampling-tube collection means for collecting one or more label pasted blood-sampling-tubes for every patient, a blood-sampling-tube transferring means for receiving the blood-sampling-tube(s) required to a blood test for the patient from the corresponding blood-sampling-tube containing section and transferring the tube(s) to the label printing and pasting unit and the blood-sampling-tube collection means, and a controller means for controlling the blood-sampling-tube containing sections, the label printing and pasting unit, the blood-sampling-tube collection means, and the blood-sampling-tube transferring means so that one or more blood-sampling-tubes required to the blood test for the patient are selectively discharged, and a label with printed information data related to the patient is pasted on the discharged blood-sampling-tube, and then the label pasted blood-sampling-tubes are discharged for every patients, wherein the each blood-sampling-tube containing section is provided with a number of compartments along a periphery thereof, in which the blood-sampling-tubes are contained one by one in a laying state, and an opening portion at a lower portion thereof for discharging the blood-sampling-tube from the each compartment, the compartments in each of the blood-sampling-tube containing section are intended to be moved in a peripheral direction thereof so that the blood-sampling-tube contained in the compartment aligned with the opening portion falls through the opening portion by moving the compartments at a suitable distance along the peripheral direction, and the blood-sampling-tube transferring means is arranged under the opening portions of the blood-sampling-tube containing sections for receiving the blood-sampling-tube felt from the each blood-sampling-tube containing section.

THE BEST MODE FOR CARRYING OUT THE INVENTION

The mode for carrying out a blood-sampling-tube preparation device according to the present invention will now be described with reference to an embodiment shown in attached drawings.

Figure 1:
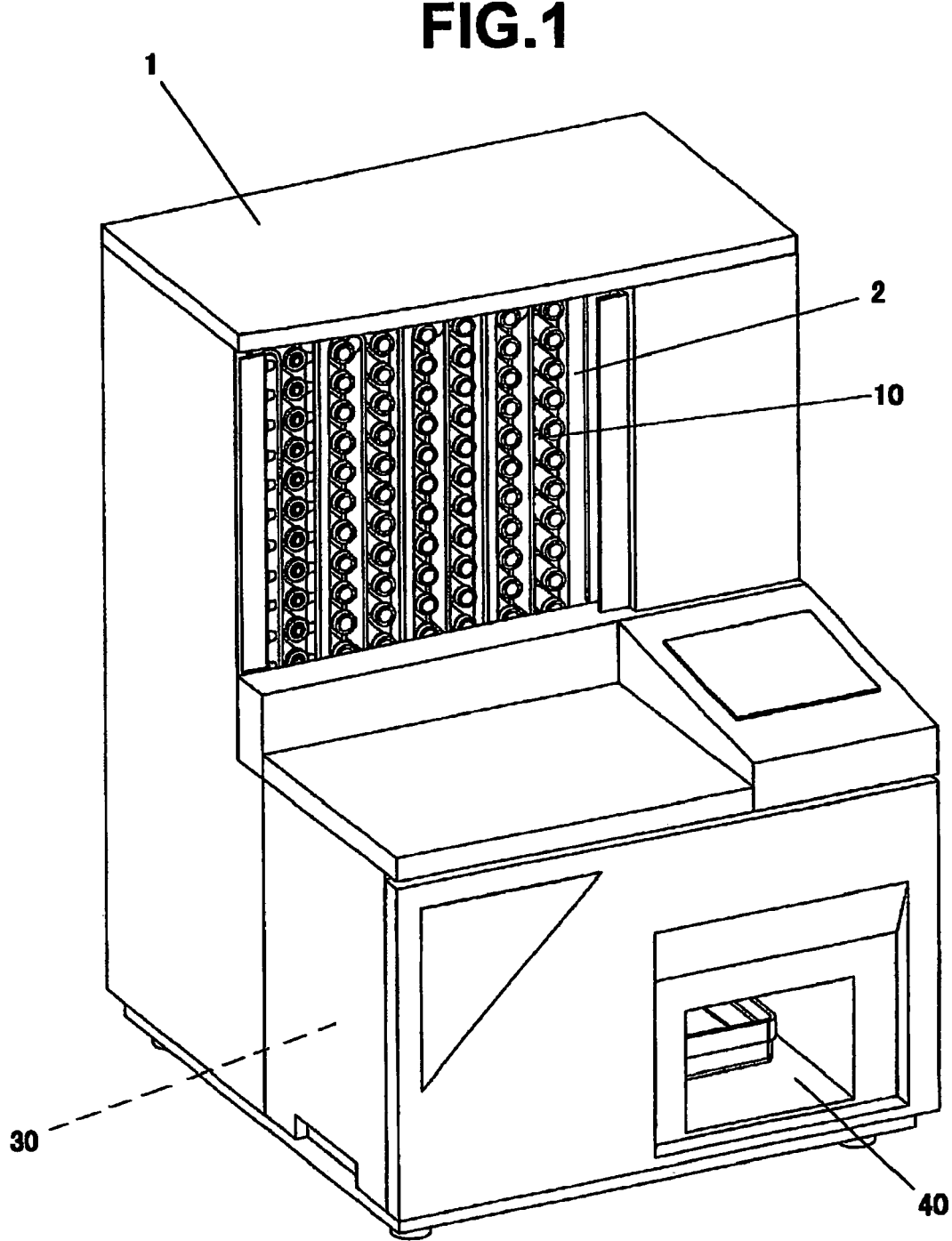
FIG. 1 is a schematic perspective view of a blood-sampling-tube preparation device according to the present invention.
Figure 2:
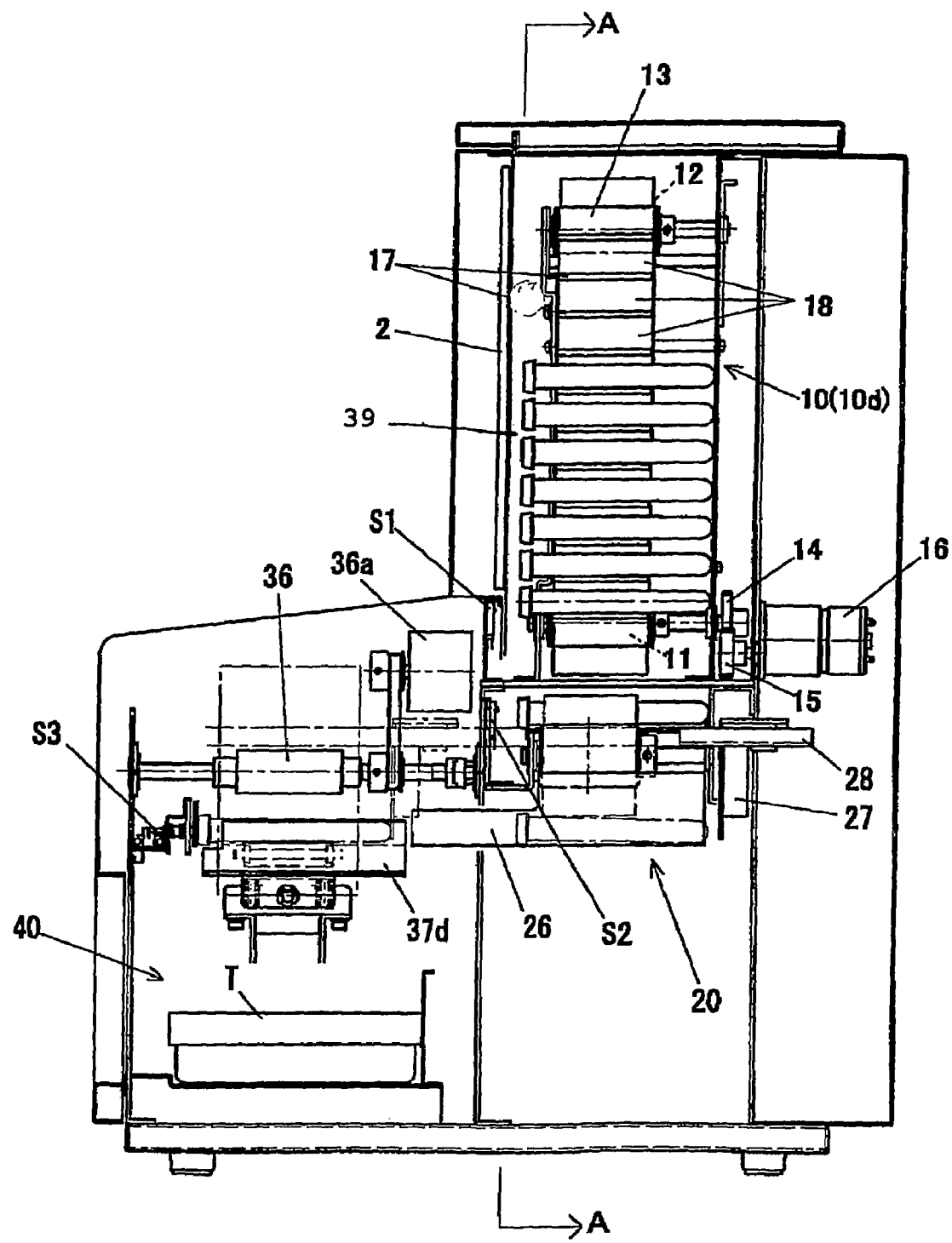
FIG. 2 is a schematic right side view showing the internal structure of the blood-sampling-tube preparation device in FIG. 1.
Figure 3:
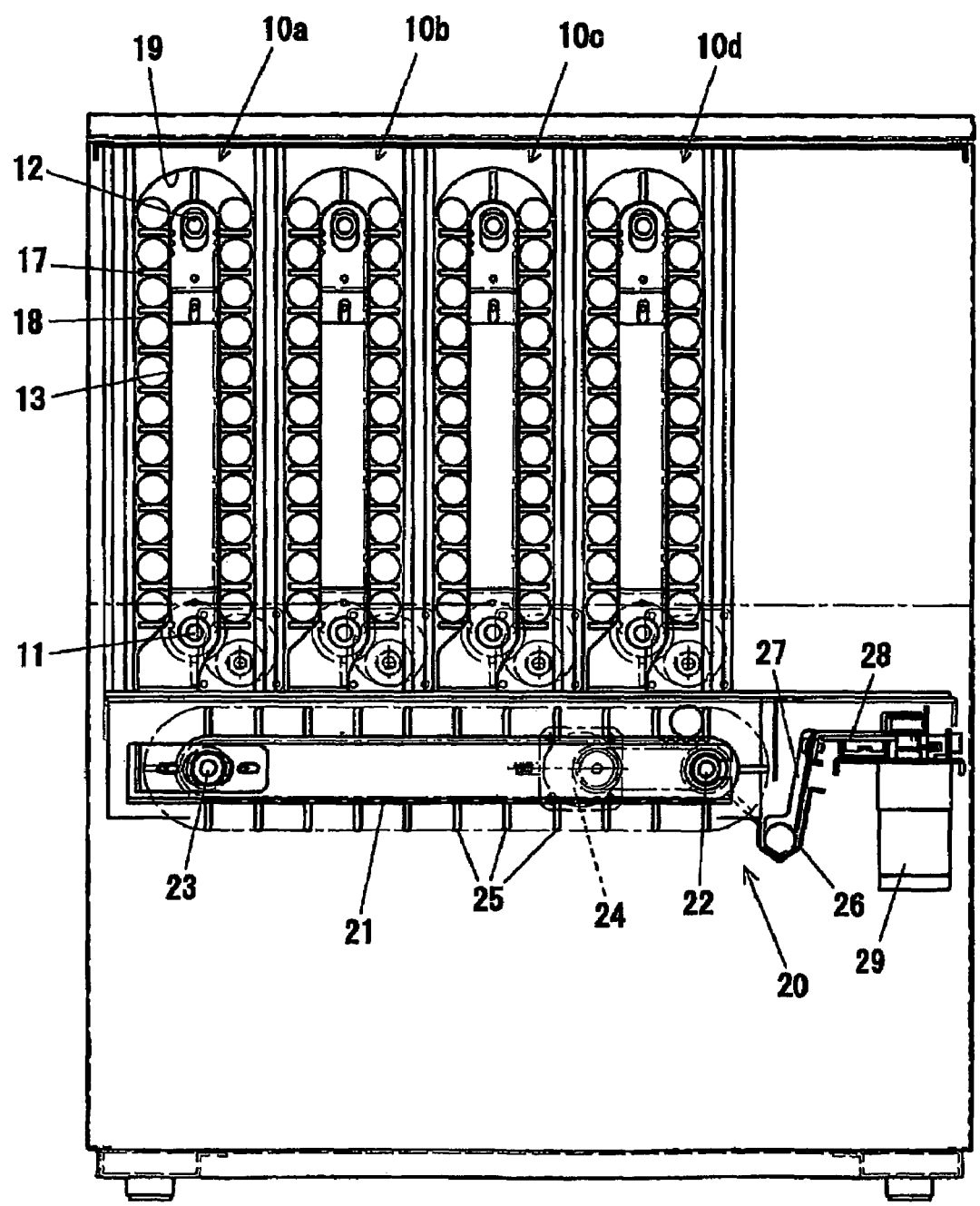
FIG. 3 is a sectional view taken along the line A-A of FIG. 2.
Figure 4:
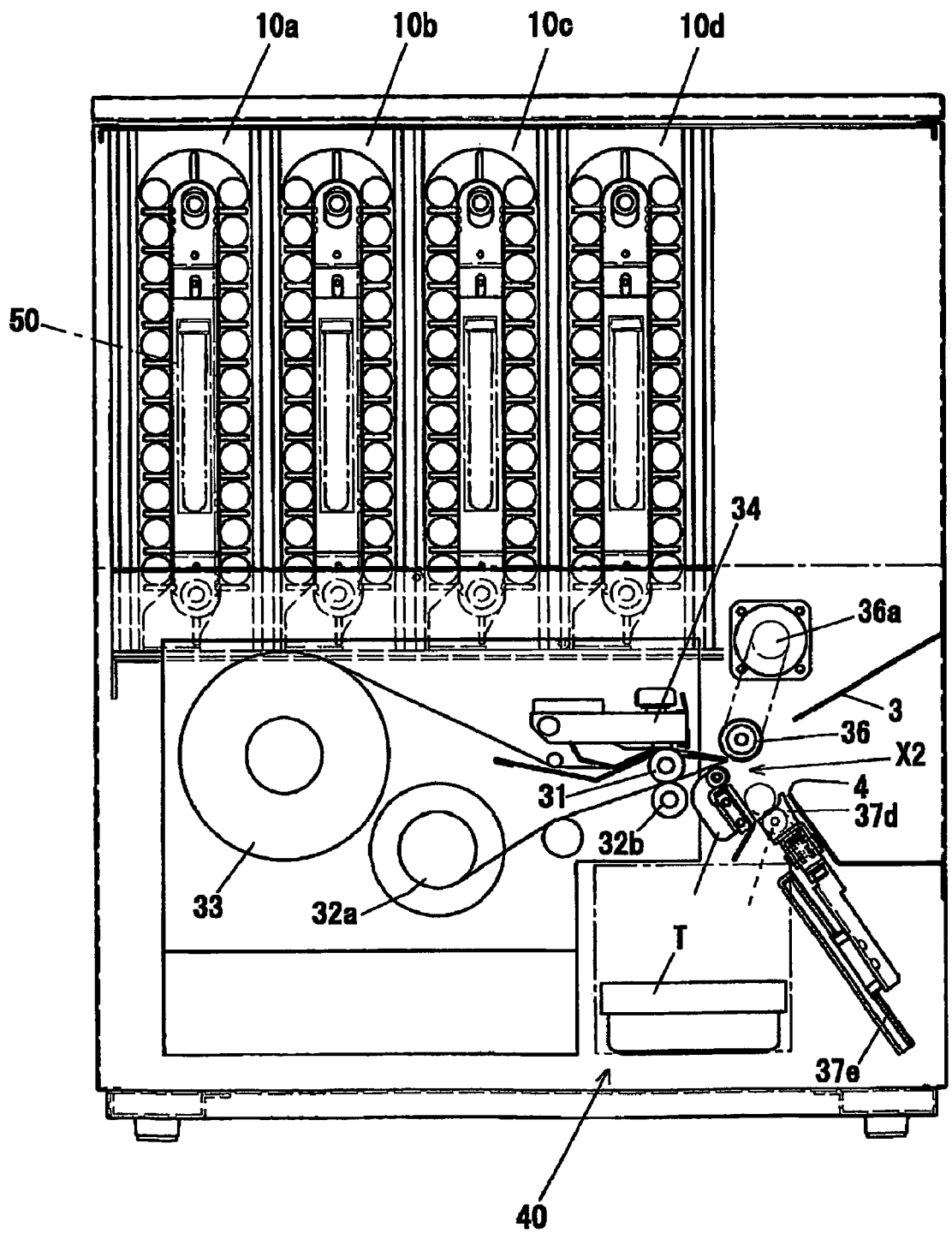
FIG. 4 is a schematic front view showing the internal structure of the blood-sampling-tube preparation device in FIG. 1.
Figure 5:
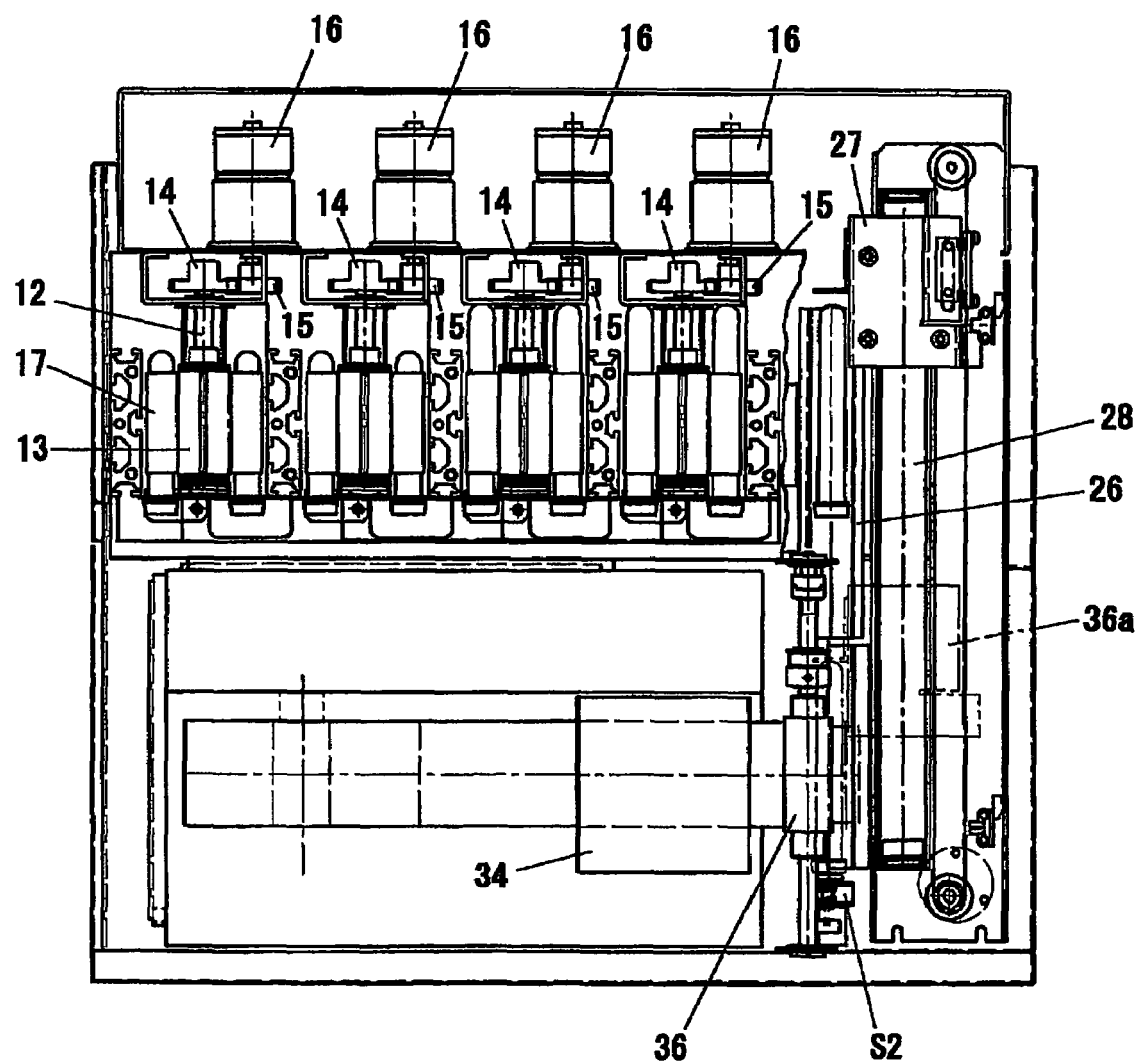
FIG. 5 is a schematic bottom view showing the internal structure of the blood-sampling-tube preparation device in FIG. 1.
Figure 6:
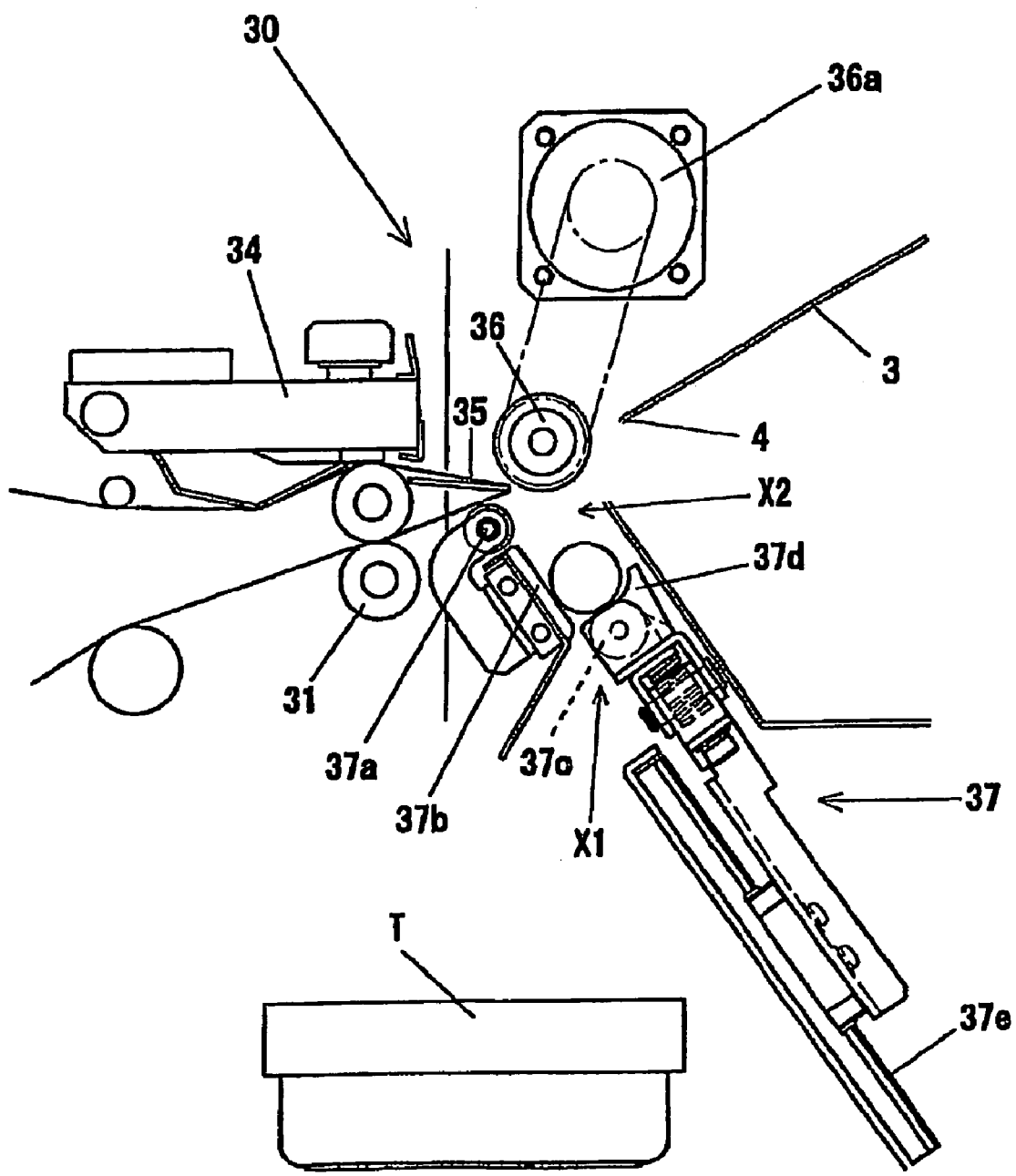
FIG. 6 is an enlarged view of the parts disposed in the vicinity of a label pasting position X2 when a pressure roller lies in a waiting position X1.

FIG. 1 is a schematic perspective view of a blood-sampling-tube preparation device according to the present invention, FIG. 2 is a schematic right side view showing the internal structure of the blood-sampling-tube preparation device in FIG. 1, FIG. 3 is a sectional view taken along the line A-A of FIG. 2, FIG. 4 is a schematic front view showing the internal structure of the blood-sampling-tube preparation device in FIG. 1, and FIG. 5 is a schematic bottom view showing the internal structure of the blood-sampling-tube preparation device in FIG. 1.

As shown in the drawings the blood-sampling-tube preparation device comprises a housing 1 in which four blood-sampling-tube containing sections 10a to 10d, a blood-sampling-tube transferring means 20, a label printing and pasting unit 30, and a blood-sampling-tube collection portion 40 are provided. Each of the blood-sampling-tube containing sections 10a to 10d vertically extends in the housing 1. The blood-sampling-tube transferring means 20 is arranged under the blood-sampling-tube containing sections 10. The label printing and pasting unit 30 is arranged under and in front of the blood-sampling-tube containing sections 10. The blood-sampling-tube collection portion 40 is arranged under the label printing and pasting unit 30.

Each blood-sampling-tube containing section 10 comprises a periphery wall 19 that has a lower portion opened, and a driving means arranged therein. The driving means comprises shafts 11 and 12 provided on upper and lower portions of the section 10, respectively, and an endless belt 13 engaged with the shafts 11 and 12. The lower shaft 11 is driven through a driven gear 14 and a driving gear 15 by a motor 16, so that the endless belt 13 is rotated. A number of partition plates 17 are integrally provided on an outer surface of the endless belt 13 with the fixed interval. Each partition plate 17 extends outwardly and in a direction perpendicular to the outer surface of the endless belt 17. On the outer surface of the belt 13, a number of compartments 18 are defined between the adjacent partition plates 17, respectively. Each of the compartments 18 contains one blood-sampling-tube.

In each of the above-mentioned blood-sampling-tube containing sections 10, the motor 16 is driven by a controller means not shown in the drawings so that the endless belt 13 is rotated in a clockwise direction in FIG. 3. When the endless belt 13 passes around the lower shaft 11, the blood-sampling-tube contained in the compartment 18 falls to the blood-containing transferring means 20 through the lower opening portion of the periphery wall 19.

In FIG. 2 a reference character S1 designates tube detecting sensors. Each of the tube detecting sensors S1 is provided on the corresponding blood-sampling-tube containing section 10. Each sensor S1 detects the blood-sampling-tube in a first compartment 18 immediately adjacent to a second compartment 18 being in a position from which the blood-sampling-tube falls to the transferring means 20. The endless belt 13 of each blood-sampling-tube containing section 10a to 10d is rotated until each of the tube detecting sensors detects the blood-sampling-tube. Therefore, each blood-sampling-tube containing section 10 is always intended to keep the blood-sampling-tube in the first compartment 18 immediately adjacent to the second compartment 18 being in position from which the blood-sampling-tube falls to the transferring means 20, even if there is any of the compartments 18 that are not charged with the tube. Thus, if necessary, the tube can be discharged by moving the belt 13 through one compartment.

The blood-sampling-tube transferring means 20 comprises an endless belt 21. The endless belt 21 is horizontally arranged under and along the four blood-collecting containing sections 10. The endless belt 21 is engaged with shafts 22 and 23 that are arranged on right and left portions thereof, respectively. The right side shaft 22 is driven through a conveyance belt (unsigned) by a motor 24, so that the endless belt 21 is rotated in a clockwise direction in FIG. 3. A number of partition plates 25 are integrally provided on an outer surface of the endless belt 21 with the fixed interval. Each of the partition plates 25 extends outwardly and in a direction perpendicular to the outer surface of the endless belt 21. One blood-sampling-tube is received between the adjacent partition plates 25.

The blood-sampling-tube transferring means 20 also comprises a guide member 26 for guiding the transferring of tube. The guide member 26 is arranged under the right side of the endless belt 21 in FIG. 3. The guide member 26 extends to the front of the device in a horizontal direction perpendicular to the endless belt 21.

The guide member 26 is provided with a plate 27 for transferring the tube. The plate 27 may be moved to backward and forward along a guide rail 28 for guiding the transferring of tube in the guide member 26 by a motor 29. The blood-sampling-tube received on the guide member 26 is pushed out to a waiting position X1 in the label printing and pasting unit 30 arranged in front of the guide member 26 by the plate 27.

In the above mentioned blood-sampling-tube transferring means 20, the blood-sampling-tube discharged from the blood-sampling-tube containing section 10 is received between the corresponding adjacent partition plates 25 and 25, and then the endless belt 21 is rotated in a clockwise direction in FIG. 3 by the motor 24. When the endless belt 21 passes around the right shaft 22, the blood-sampling-tube supported between the adjacent partition plates 25 and 25 falls to the guide member 26.

After the blood-sampling-tube falls to the guide member 26, the plate 27 is moved forward by the motor 29 so that the blood-sampling-tube is pushed out to the waiting position X1 arranged in front of the guide member 26. And then the plate 27 is moved to the most rear position of the guide member 26 and is kept at that position until the next blood-sampling-tube falls on the guide member 26.

In FIG. 2 a reference character S2 designates a tube detecting sensor that is provided on a portion of the device corresponding to a right side portion of the endless belt 21. The tube detecting sensor S2 detects the blood-sampling-tube in a first compartment defined between the adjacent partition plates 25 and 25 immediately adjacent to a second compartment defined between the adjacent partition plates 25 and 25 being in a position from which the blood-sampling-tube falls onto the guide member 26. After the endless belt 21 receives the blood-sampling-tube from the blood-sampling-tube containing section, the endless belt 21 is rotated until the tube detecting sensor S2 detects the blood-sampling-tube. The blood-sampling-tube is kept at the position where the tube detecting sensor S2 detects the blood-sampling-tube, and then the tube is dropped onto the guide member 26 by further rotating the endless belt 21 at the desirable timing. Therefore, in the case that a number of tubes are continuously handled in the device, while a previous tube is handled, a next tube is transferred to a position of the endless belt 21 immediately adjacent to a position of the endless belt 21 from which the blood-sampling-tube falls onto the guide member 26 and is kept at that position. Therefore, the processing efficiency of the device becomes high.

The label printing and pasting unit 30 comprises a platen roller 31 and rollers 32a and 32b. The drive rollers 32a and 32b are rotated in synchronization with the platen roller 31. A label mount is drawn from a label mount roll 33 by rotating the rollers 31, 32a and 32b. A print head 34 prints patient information data corresponding to the blood-sampling-tube on which the label 38 is to be pasted, on the label mounted on the label mount that was drawn from the roll 33 according to the data send from the controller means not shown in drawings. The printed label 38 is separated from the label mount by bending the label mount to an acute angle against a direction of the travel of the label mount by a separation plate 35. The separated label 38 is pasted on the blood-sampling-tube rotating at the label pasting portion X2 near the tip of the separation plate 35.

A pasting roller 36 is a part of the label printing and pasting unit and is arranged above the label pasting position X2. A blood-sampling-tube pressing and discharging means 37 forms a part of both of the label printing and pasting unit 30 and the blood-sampling-tube transferring means 20 and is arranged under the label-pasting position X2.

The blood-sampling-tube pressing and discharging means 37 comprises a supporting roller 37a, a waiting rack 37b, a pressure rack 37d and a guide rail 37e. The supporting roller 37a supports the blood-sampling-tube at the label-pasting position X2. The waiting rack 37b supports the blood-sampling-tube at the waiting position X1. The pressure rack 37d has a pressure roller 37c. The pressure roller 37c pushes up the blood-sampling-tube from the waiting position X1 to the label-pasting position X2, and then presses the blood-sampling-tube toward the pasting roller 36 at the label-pasting position X2. The guide rail 37e guides the pressure roller 37c that is movable between the waiting position X1, the label-pasting position X2, the blood-sampling-tube discharging position X3, and the label-discharging position X4.

In FIG. 2 a reference character S3 designates a sensor for detecting the arriving of tube. The sensor S3 is arranged on the extension line of the guide member 26. When the blood-sampling-tube is pushed out to the waiting position X1 by the plate 27, the head of the blood-sampling-tube contacts to the sensor S3, and the sensor S3 detects the arriving of the blood-sampling-tube. And then the pressure roller 37c of the blood-sampling-tube pressing and discharging means 37 pushes up the blood-sampling-tube to the label-pasting position X2.

The blood-sampling-tube collection means 40 may include a tray T in the inside thereof. The tray T arranged in the collection means 40 receives the label pasted blood-sampling-tube discharged through a blood-sampling-tube outlet 27a.

Finally, the construction of the housing 1 that contains each of the above-mentioned members in the inside thereof will be described. The housing 1 is provided with a front cover 2 at a portion being in front of the blood-sampling-tube containing section 2 thereof. The front cover 2 can open and close. The front cover 2 is transparent in order to identify the types of the blood-sampling-tubes contained in each containing section 10a to 10d in use at first sight.

Hereinafter blood-sampling-tubes will be briefly explained. Recently, there are many cases that vacuum blood-sampling-tubes are used as the blood-sampling-tubes for drawing blood. The vacuum blood-sampling-tubes are sealed up in the state that reaction liquid was put into inside, in order to maintain internal negative pressure. Colors of caps of the vacuum blood-sampling-tubes are changed according to the types of the vacuum blood-sampling-tubes in order to identify what blood test is the vacuum blood-sampling-tube for.

In the above mentioned blood-sampling-tube preparation device, the vacuum blood-sampling-tubes are contained in the blood-sampling-tube containing section 10 so that the caps of the tubes are directed to the front of the device, and the door 2 arranged in front of the sections 10 is transparent. Therefore, it is possible to see the colors of the blood-sampling-tubes from the outside. And also in use, a user is able to identify the types of blood-sampling-tubes contained in the each blood-sampling-tube containing section 10 at first sight. Also the user is able to check whether or not the tubes different from the intended tubes are contained in the blood-sampling-tube containing sections 10. And also the user is able to check the number of remains of the blood-sampling-tubes in the blood-sampling-tube containing sections 10, at first sight.

Also in the above mentioned blood-sampling-tube preparation device, each of the blood-sampling-tube containing sections 10 is partitioned to a number of compartments and each of the compartments contains one blood-sampling-tube therein. And in the device, a blood-sampling-tube supplementation section 39 is exposed in front of the device. Therefore, it is possible to replenish the blood-sampling-tube containing sections with new blood-sampling-tubes in use.

On a right side plate of the housing 1 in FIG. 1, a concave portion 3 is formed. The concave portion 3 faces the label pasting position X2 and is dented to near the label pasting position X2. An opening 4 for taking the label 38 out is provided on the concave portion 3 (See FIG. 4 and FIGS. 6 to 9).

Here, the structure of the parts disposed in the vicinity of the label pasting position X2 of the label printing and pasting unit 30 will be described again. As shown in FIG. 4, the parts 31 to 35 of the label printing and pasting unit 30 are arranged at the left side of the label pasting position X2. The pasting roller 36 is arranged above the label pasting position X2 and the blood-sampling-tube pressing and discharging means 37 is arranged under the label-pasting position X2. Therefore, there no parts is arranged at the right side of the label pasting position X2, that is to say no parts is arranged on a traveling path of the label 38 separated from the mount. The opening 4 is formed on the right side plate of the housing 1 through which the label 38 separated from the mount may be passed. The label printing and pasting unit 30 may be operated even if there is no blood-sampling-tube in the label-pasting position X2. The pressure roller 37c may be made of any non-adhesive material or may have a surface provided with a number of grooves, in order to prevent the label 38 from pasting on the surface of the pressure roller 37c.

Since the blood-sampling-tube preparation device is constructed as described above, if one or more blood-sampling-tubes of the kinds that are not contained in the blood-sampling-tube containing sections 10 are used in the blood test, the label printing and pasting unit 30 is operated without the blood-sampling-tube at the label-pasting position X2 so that information data for a patient is printed on a label 38, and then the printed label 38 is separated from the mount, and finally the separated label 38 is discharged through the opening 4.

The function of the above mentioned blood-sampling-tube preparation device will now be explained.

At first, user puts the intended blood-sampling-tubes into the blood-sampling-tube containing sections 10a to 10d, respectively. Same kind of the blood-sampling-tubes are contained in the same blood-sampling-tube containing section 10. The kinds of the blood-sampling-tubes contained in the blood-sampling-tube containing sections 10a to 10d are previously registered to the controller means (or whenever the blood-sampling-tubes are contained into each blood-sampling-tube containing section 10a to 10d).

Here, how to put the blood-sampling-tubes into the blood-sampling-tube containing sections 10 will be briefly explained. At first user opens the front cover 2, and then puts the intended blood-sampling-tubes one by one between the adjacent partition plates 14 and 14 i.e. each compartment 18 of the corresponding blood-sampling-tube containing section 10a to 10d, so that the caps of the tubes are directed to the front of the blood-sampling-tube preparation device (that is to say the caps of the tubes are directed to the front cover 2). The types of the blood-sampling-tubes contained in the each blood-sampling-tube containing section 10a to 10d are directly input to the controller means which is for example a computer or the like. Alternatively, an operation panel may be provided on the blood-sampling-tube preparation device, and the data related to the change of the types of the blood-sampling-tubes contained the blood-sampling-tube containing sections 10 may be input via the panel to the controller means. Also buttons corresponding to the types of the blood-sampling-tubes that are used very often may be provided on each blood-sampling-tube containing section 10 of the blood-sampling-tube preparation device, if user changes the kinds of the blood-sampling-tubes to be contained in the blood-sampling-tube containing sections, the data related to the change of the types of the blood-sampling-tubes may be transferred to the controller means by means of the buttons.

It is possible to see the caps of the blood-sampling-tubes contained the blood-sampling-tube containing sections 10 from out side at first sight, because the blood-sampling-tubes are put into the blood-sampling-tube containing sections 10 so that the caps of the blood-sampling-tubes are directed to the front of the device. Additionally, a marker containing section 50 (that are indicated in FIG. 4 by dashed lines) which contains the blood-sampling-tube as marker may be provided in the inside area surrounded by each of the endless belts 13.

By means of providing the marker containing sections 50 each of which contains the blood-sampling-tube as a mark, it is possible to identify the kinds of the blood-sampling-tubes contained the blood-sampling-tube containing sections 10 more easily.

Again, the function of the blood-sampling-tube preparation device will be described. The blood-sampling-tube preparation device receives the information data related to the patient to be printed the label 38 and related to the kinds of the blood-sampling-tubes to be used in the blood test of the patient. And then on the basis of the information data, the endless belt 13 of the blood-sampling-tube containing section 10 which contains the blood-sampling-tube of the kind required in the blood test of the patient is rotated, so that one blood-sampling-tube is discharged to the endless belt 21 of the blood-sampling-tube transferring means 20 from the blood-sampling-tube containing section 10.

After the discharged tube is received between the adjacent partition plates 25 and 25 of the endless belt 21, the endless belt 21 of the blood-sampling-tube transferring means 20 is rotated in the clockwise direction, so that the tube falls on to the guide member 26.

After the tube falls onto the guide member 26, the tube is pushed out by the plate 27 to the waiting position X1 arranged in front of the guide member 26.

Figure 7:
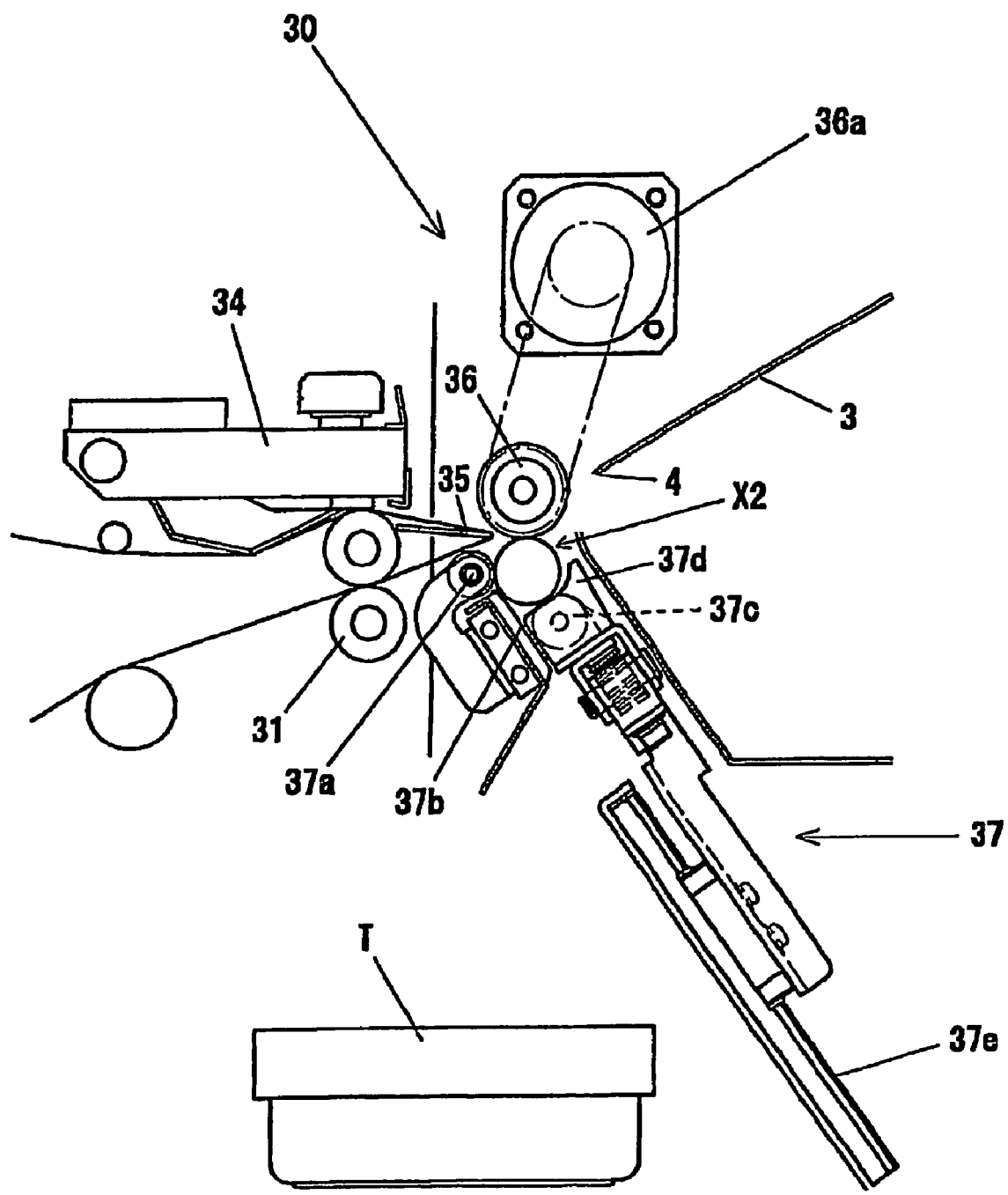
FIG. 7 is an enlarged view of the parts disposed in the vicinity of the label pasting position X2 when the pressure roller lies in the label pasting position X2.
Figure 8:
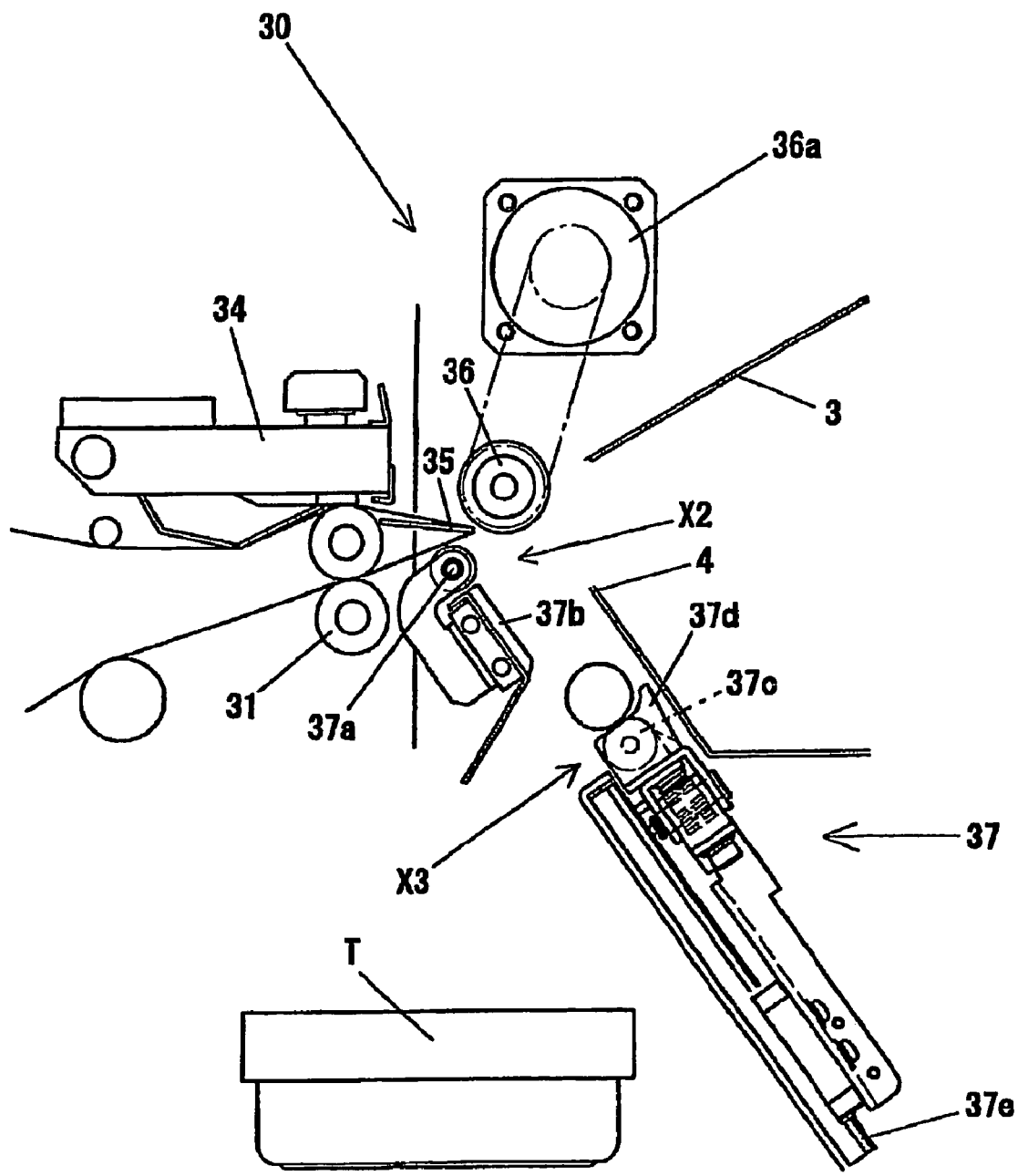
FIG. 8 is an enlarged view of the parts disposed in the vicinity of the label pasting position X2 when the pressure roller lies in a tube discharging position X3.
Figure 9:
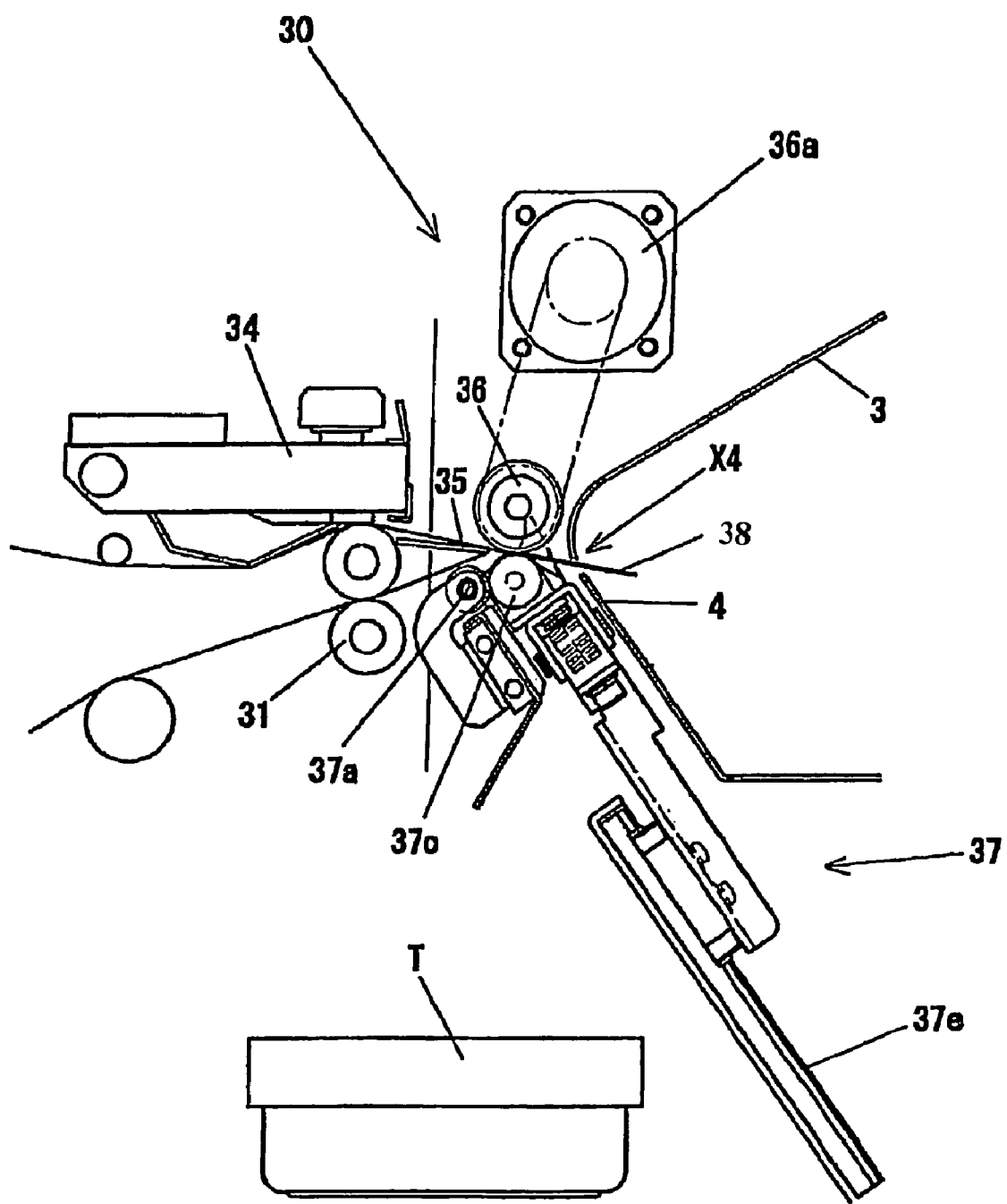
FIG. 9 is an enlarged view of the parts disposed in the vicinity of the label pasting position X2 when the pressure roller lies in a label discharging position X4.

After the tube is pushed out to the waiting position X1, as shown in FIG. 7, the tube is pushed up to the label-pasting position X2 by the pressure roller 37c. In the label pasting position X2, the tube is supported at three points by the pasting roller 36, the supporting roller 37a and the pressure roller 37c, and is rotated by the pasting roller 36.

The label 38 on which the information data related to the patient is printed is separated from the mount by the separation plate 35 and then the label 38 contacts with the blood-sampling-tube rotated in the label pasting position X2, and then the label 38 is pasted on the blood-sampling-tube by the pasting roller 36.

After the label 38 is pasted on the blood-sampling-tube, the pressure roller 37c on which the label pasted tube is carried is moved downward. When the pressure roller 37c reaches the blood-sampling-tube discharging position X3, the label pasted tube falls into the tray T arranged in the blood-sampling-tube collection means 40 (See FIG. 8).

In the case that it is necessary to paste the label 38 on the blood-sampling-tube of the kind that is not contained in the blood-sampling-tube containing sections 10, the label printing and pasting unit 30 is operated without the tube in the label pasting position X2. More concretely, in this case, the pressure roller 37c is moved upward to the label discharging position X4, and then the printed label 38 is transferred to the opening 4 by the pasting roller 36 and the pressure roller 37c, and finally the printed label 38 is discharged through the opening 4.

The above-mentioned processes are repeated continuously label(s) 38 is pasted on the all tube(s) required to the blood test for the patient and the tube(s) is discharged from the device to the tray T. After that, the blood-sampling-tube preparation device is stopped.

The operation timing of the blood-sampling-tube containing section 10, the blood-sampling-tube transferring means 20 and the label printing and pasting unit 30 are suitably set up so as to prevent the tubes from hitting each other in use, and to prevent the tubes for the unintended patient from entering into the tray T for containing the tubes for the intended patient.

More concretely, for example, these elements may be driven as follows. After a first blood-sampling-tube falls onto the guide member 26 from the endless belt 21 of the tube transferring means 20, the blood-sampling-tube containing section 10 is driven so that a second blood-sampling-tube falls onto the endless belt 21 from the containing section 10. And then the second blood-sampling-tube on the endless belt 21 is transferred to the right end of the endless belt 21 and is maintained in that position. After the first tube is pushed out to the label-pasting position X2 by the plate 26 and the plate 26 is returned to the most rear position of the guide member 26, the second tube falls onto the tube transferring guide member 26.

If blood-sampling-tubes for a number of patients are continuously processed in the blood-sampling-tube preparation device, after the blood-sampling-tube(s) for a first patient is completely processed, the blood-sampling-tube(s) for next patient is kept at the blood-sampling-tube containing section, the blood-sampling-tube transferring means and/or the label printing and pasting unit, until the tray T is exchanged.

In the above-mentioned embodiment, one tray T is arranged in the blood-sampling-tube collection means 40 and a user carries out the exchange of the tray arranged in the collection means 40. However the construction of the blood-sampling-tube collection means 40 is not restricted to the above embodiment. For example, an empty tray stock means in which a number of empty trays T are arranged in a superposed relationship or a row, a tray collection means in which a number of trays T containing one or more label pasted therein tube are arranged in a superposed relationship or a row, and a tray transferring means for transferring the tray T from the empty tray stock means to the tray collection means through a blood-sampling-tube collection portion in which one or more label pasted tubes are collected into the tray T may be provided on or in the blood-sampling-tube preparation device. In this case, after the label pasted tube(s) for one patient is completely collected in a tray T, the tray T in which the label pasted tube(s) is collected may be transferred from the blood-sampling-tube collection portion to the tray collection means by the tray transferring means and an empty tray T may be transferred from the empty tray stock means to the blood-sampling-tube collection portion by the tray transferring means.

Also, in the above embodiment, one tray T is arranged in the blood-sampling-tube collection means 40 and the blood-sampling-tube(s) is collected in the tray T. However the construction of the blood-sampling-tube collection means 40 is not restricted to the embodiment. For example, the blood-sampling-tube collection means may be constructed to include a bag therein, and the label pasted tube(s) may be collected in the bag.

Further, in the above embodiment, each of the blood-sampling-tube containing sections 10 comprises the endless belt 13 engaged with the upper and lower shafts 11 and 12, and a number of partition plates 17 integrally provided on the surface of the endless belt 13, and each of the blood-sampling-tubes is contained in the compartment defined between the adjacent partition plates 17. However the construction of the blood-sampling-tube containing section 10 is not restricted to the embodiment. For example, a circular disk having a certain thickness can construct a blood-sampling-tube containing section. In this case, a number of grooves are formed on a circumference of the circular disk, and each of the grooves defines a compartment in which a blood-sampling-tube is contained.

Also, in the above embodiment, each of the blood-sampling-tube containing section 10 vertically extends in the housing 1 and all of the containing sections 10 are disposed in a lateral direction in FIGS. 3 and 4. However the arrangement of the blood-sampling-tube containing sections 10 is not restricted to the embodiment. For example, all of the containing sections 10 may be disposed in a cross direction in the FIGS. 3 and 4.

Further, in the above embodiment, the blood-sampling-tube preparation device comprises four blood-sampling-tube containing sections 10, thus four kinds of blood-sampling-tubes at maximum may be contained in the blood-sampling-tube containing sections 10. However, the number of the blood-sampling-tube containing section 10 may be freely selected without being restricted to the embodiment.

Also in the above embodiment, the label printing and pasting unit 30 is arranged under the front of the blood-sampling-tube containing sections 10 and the blood-sampling-tube collection means 40 is arranged under the label printing and pasting unit 30. However the arrangement of these means is not restricted to the embodiment. For example, the label printing and pasting unit 30 may be arranged just under blood-sampling-tube containing sections 10, and the blood-sampling-tube collection means 40 may be arranged just under the label printing and pasting unit 30. In this case, since the blood-sampling-tube containing sections 10, the label printing and pasting unit 30 and the blood-sampling-tube collection means 40 are arranged in a superposed relationship, a posterior-anterior width of the blood-sampling-tube preparation device becomes shorter, and therefore a space for setting the blood-sampling-tube preparation device becomes smaller. Also in said arrangement, since a moving distance of the blood-sampling-tube becomes very short and the blood-sampling-tube transferring means 20 can be structurally simplified, a processing speed of the device becomes faster and a possibility that the blood-sampling-tube(s) will be caught in a belt of the transferring means 20 during operation may be reduced.

INDUSTRIAL APPLICABILITY

As described above, in the blood-sampling-tube preparation device according to the present invention, the each blood-sampling-tube containing section is provided with a number of compartments along a periphery thereof, in which the blood-sampling-tubes are contained one by one in a laying state, and an opening portion at a lower portion thereof for discharging the blood-sampling-tube from the each compartment, the compartments in each of the blood-sampling-tube containing section are intended to be moved in a peripheral direction thereof so that the blood-sampling-tube contained in the compartment aligned with the opening portion falls through the opening portion by moving the compartments at a suitable distance along the peripheral direction, and the blood-sampling-tube transferring means is arranged under the opening portions of the blood-sampling-tube containing sections for receiving the blood-sampling-tube felt from the each blood-sampling-tube containing section. Therefore, it is not necessary to provide a complicated mechanism for taking out the blood-sampling-tube from the blood-sampling-tube containing section. And therefore, the blood-sampling-tube preparation device can be structurally simplified and miniaturized.

And in the blood-sampling-tube preparation device according to the present invention, each of the blood-sampling-tube containing sections is longitudinally and vertically extended, all of the blood-sampling-tube containing sections are arranged in a row, and at least a part of the blood-sampling-tube transferring means is arranged under and along the blood-sampling-tube containing sections. Therefore the blood-sampling-tube transferring means can be miniaturized.

Further, in the blood-sampling-tube preparation device according to the present invention, each of the blood-sampling-tube containing sections includes a blood-sampling-tube supplementation section that is exposed in front of the device, and each of the blood-sampling-tubes is put into the compartment so that a cap of the blood-sampling-tube is directed to the front of the device. Therefore, in use, a user can identify the number of remains and the types of the blood-sampling-tube contained in the blood-sampling-tube containing sections from the outside at first sight. Also the user can check whether or not the tubes different from the intended tubes are contained in the blood-sampling-tube containing sections.

Further more, in the blood-sampling-tube preparation device according to the present invention, the blood-sampling-tube transferring means and the label printing and pasting unit are arranged under the blood-sampling-tube containing means, and the blood-sampling-tube collection means is arranged under the label printing and pasting unit. Therefore, the blood-sampling-tube containing section, the label printing and pasting unit, and the blood-sampling-tube collection means may be effectively and compactly arranged. And therefore, the blood-sampling-tube preparation device can be miniaturized.

Also, in the blood-sampling-tube preparation device according to the present invention, each of the blood-sampling-tube containing sections includes a maker containing portion in the inside thereof, in which a blood-sampling-tube as a marker is vertically contained. Therefore, it is possible to identify the kinds of the blood-sampling-tubes contained the blood-sampling-tube containing section 10 more easily.

Further, in the blood-sampling-tube preparation device according to the present invention, the blood-sampling-tube containing sections, the blood-sampling-tube transferring means, the label printing and pasting unit, and the blood-sampling-tube collection means are contained in a housing in which the label printing and pasting unit is arranged so that a forward end of a traveling path of the label separated from a label mount is opened, and the housing is provided with an opening through which the label separated from the label mount passes, so that when there is no blood-sampling-tube in a label pasting position of the label printing and pasting unit, the printed label separated form the label mount is discharged through the opening. Therefore, even if it is necessary to paste the label on the blood-sampling-tube of the kind that is not contained in the blood-sampling-tube containing sections, since the separated label on which the information data related to the patient is discharged from the device through the opening, the user easily pastes the printed label on the tube which is not contained the blood-sampling-tube containing section.

The invention claimed is:

1. A blood-sampling-tube preparation device comprising
at least two blood-sampling-tube containing sections, each of the sections being intended to contain same kind of blood-sampling-tubes according to sorts thereof,
a label printing and pasting unit for printing information data related to a patient on a label and for pasting the printed label on the blood-sampling-tube,
a blood-sampling-tube collection means for collecting one or more label pasted blood-sampling-tubes for every patient,
a blood-sampling-tube transferring means for receiving the blood-sampling-tube(s) required for a blood test for the patient from the corresponding blood-sampling-tube containing section and transferring the tube(s) to the label printing and pasting unit and the blood-sampling-tube collection means, and
a controller means for controlling the blood-sampling-tube containing sections, the label printing and pasting unit, the blood-sampling-tube collection means, and the blood-sampling-tube transferring means so that one or more blood-sampling-tubes required for the blood test for the patient are selectively discharged, and the label with printed information data related to the patient is pasted on the discharged blood-sampling-tube, and then the label pasted blood-sampling-tubes are discharged for every patients,
wherein each of the blood-sampling-tube containing sections is provided with a plurality of compartments along a periphery thereof, in which the blood-sampling-tubes are separated one from another in a laying state, and an opening portion at a lower portion thereof for discharging the blood-sampling-tube from the each of said compartments,
the compartments in each of the blood-sampling-tube containing section are movable in a peripheral direction thereof so that the blood-sampling-tube contained in the compartment aligned with the opening portion falls through the opening portion by moving the compartments a suitable distance along the peripheral direction,
the blood-sampling-tube transferring means is arranged under the opening portions of the blood-sampling-tube containing sections for receiving the blood-sampling-tube that falls from the each blood-sampling-tube containing section,
each of the blood-sampling-tube containing sections includes a blood-sampling-tube supplementation section that is exposed in front of the device so that the blood-sampling-tubes can be replenished, and
each of the blood-sampling-tubes is put into the compartment so that a cap of the blood-sampling-tube is directed to the front of the device;
wherein
each of the blood-sampling-tube containing sections is longitudinally and vertically extended,
all of the blood-sampling-tube containing sections are aligned and arranged in a row, and
the blood-sampling-tube transferring means comprises an endless belt, and
said endless belt is arranged under and along the blood-sampling-tube containing sections and has a length extending over an area where the blood-sampling-tube containing sections are provided.

2. The blood-sampling-tube preparation device according to claim 1,
wherein the blood-sampling-tube transferring means and the label printing and pasting unit are arranged under the blood-sampling-tube containing means, and
the blood-sampling-tube collection means is arranged under the label printing and pasting unit.

3. The blood-sampling-tube preparation device according to claim 1,
wherein each of the blood-sampling-tube containing sections includes a marker containing portion in the inside thereof, in which a blood-sampling-tube as a marker is vertically contained.

4. The blood-sampling-tube preparation device according to claim 1, wherein
the blood-sampling-tube containing sections, the blood-sampling-tube transferring means, the label printing and pasting unit, and the blood-sampling-tube collection means are contained in a housing in which the label printing and pasting unit is arranged so that a forward end of a traveling path of the label separated from a label mount is opened, and the housing is provided with an opening through which the label separated from the label mount passes, so that when there is no blood-sampling-tube in a label pasting position of the label printing and pasting unit, the printed label separated form the label mount is discharged through the opening.

5. The blood-sampling-tube preparation device according to claim 4,
wherein the label printing and pasting unit comprises
a label pasting roller for rotating the blood-sampling-tube at the label pasting position of the label printing and pasting unit, and
a blood-sampling-tube pressing roller for pressing the blood-sampling-tube toward the label pasting roller so that the label separated from the mount progresses forward without being interfered by the label pasting roller and the blood-sampling-tube pressing roller and therefore the forward end of the traveling path of the label separated from the label mount is opened,
wherein the housing is provided with the opening through which the label separated from the label mount passes, and
the blood-sampling-tube pressing roller is intended to be moved to a portion where the blood-sampling-tube pressing roller contacts with the label pasting roller, so that when there is no blood-sampling-tube in the label pasting position of the label printing and pasting unit, only the printed label separated form the label mount is discharged through the opening.

6. The blood-sampling-tube preparation device according to claim 5,
wherein the blood-sampling-tube pressing roller is made of the non-adhesive material.

7. The blood-sampling-tube preparation device according to claim 5, wherein the blood-sampling-tube pressing roller has a surface provided with a number of grooves.

8. The blood-sampling-tube preparation device according to claim 1, wherein the blood-sampling-tube transferring means is provided with a plurality of partitions along a periphery thereof, between each two of the partitions a space is provided to contain one blood-sampling-tube.

9. The blood-sampling-tube preparation device according to claim 1, wherein a controller means further comprises one or multiple detecting sensors for detecting the presence and/or the type of a blood-sampling-tube in a individual compartment of the blood-sampling-tube containing section, on the blood-sampling-tube transferring means and/or at the label printing and pasting unit, to coordinate the blood-sampling-tube containing section, the blood-sampling-tube transferring means and the label printing and pasting unit so that one or more blood-sampling-tubes required to the blood test for the patient are selectively discharged, and the label with printed information data related to the patient is pasted on the discharged blood-sampling-tube, and then the label pasted blood-sampling-tubes are discharged for respective patients.

10. The blood-sampling-tube preparation device according to claim 1, wherein
the label printing and pasting unit is arranged on a side of said endless belt of the blood-sampling-tube transferring means.

11. The blood-sampling-tube preparation device according to claim 1, wherein
the blood-sampling-tube containing sections, the blood-sampling-tube transferring means, the label printing and pasting unit, and the blood-sampling-tube collection means are contained in a housing.

12. The blood-sampling-tube preparation device according to claim 11, wherein
the housing comprising a door arranged in front of the blood-sampling-tube containing section, and the door is transparent.

* * * * *